US012799232B2

(12) United States Patent
Vidal, Jr. et al.

(10) Patent No.: US 12,799,232 B2
(45) Date of Patent: Nov. 17, 2026

(54) FIBER-WASHING IN CORN WET-MILLING

(71) Applicant: Novozymes A/S, Bagsvaerd (DK)

(72) Inventors: Bernardo Vidal, Jr., Wake Forest, NC (US); Yi Cao, Beijing (CN); Oscar Pastor Ferrer, Benifaio (ES); Brian Manning, Raleigh, NC (US); Madelyn Mallison Shoup, Raleigh, NC (US); Svend Gunnar Kaasgaard, Skovlunde (DK); Mary Ann Stringer, Soborg (DK); Lorena Gonzalez Palmen, Akarp (SE)

(73) Assignee: Novozymes AIS, Bagsvaerd (DK)

( * ) Notice: Subject to any disclaimer, the term of this patent is extended or adjusted under 35 U.S.C. 154(b) by 789 days.

(21) Appl. No.: 18/010,761

(22) PCT Filed: Jul. 7, 2021

(86) PCT No.: PCT/CN2021/104908
§ 371 (c)(1),
(2) Date: Dec. 15, 2022

(87) PCT Pub. No.: WO2022/007825
PCT Pub. Date: Jan. 13, 2022

(65) Prior Publication Data

US 2023/0227585 A1 Jul. 20, 2023

(30) Foreign Application Priority Data

Jul. 9, 2020 (WO) ................ PCT/CN2020/101111

(51) Int. Cl.
*C12P 21/06* (2006.01)
*C08B 30/04* (2006.01)
*C12P 19/14* (2006.01)

(52) U.S. Cl.
CPC ............ *C08B 30/044* (2013.01); *C12P 21/06* (2013.01)

(58) Field of Classification Search
CPC ........ C08B 30/044; C12P 21/06; C12P 19/14; C12N 9/2437
See application file for complete search history.

(56) References Cited

U.S. PATENT DOCUMENTS

| | | | | |
|---|---|---|---|---|
| 5,066,218 | A | 11/1991 | Silver | |
| 6,566,125 | B2 | 5/2003 | Johnston et al. | |
| 2012/0288900 | A1 | 11/2012 | He | |
| 2014/0127760 | A1 * | 5/2014 | He | C08B 30/02 435/99 |

FOREIGN PATENT DOCUMENTS

| | | | | |
|---|---|---|---|---|
| CN | 102433368 | A | 5/2012 | |
| CN | 102433369 | A | 5/2012 | |
| CN | 103254320 | A | 8/2013 | |
| CN | 104404014 | A | 3/2015 | |
| CN | 106832009 | A | 6/2017 | |
| CN | 109456413 | A | 3/2019 | |
| CN | 109641973 | A | 4/2019 | |
| CN | 109913388 | A | 6/2019 | |
| CN | 110770283 | A | 2/2020 | |
| CN | 110981978 | A | 4/2020 | |
| CN | 111432648 | A | 7/2020 | |
| EP | 1604998 | A2 | 12/2005 | |
| WO | 2001094608 | A1 | 12/2001 | |
| WO | WO-0194608 | A1 * | 12/2001 | C12P 19/04 |
| WO | 2002000731 | A1 | 1/2002 | |
| WO | 2002000911 | A1 | 1/2002 | |
| WO | 2002002644 | A1 | 1/2002 | |
| WO | 2010011957 | A2 | 1/2010 | |
| WO | 2014082564 | A1 | 6/2014 | |
| WO | 2014082566 | A1 | 6/2014 | |
| WO | 2016095856 | A1 | 6/2016 | |
| WO | 2017088820 | A1 | 6/2017 | |
| WO | 2018053220 | A1 | 3/2018 | |
| WO | 2018095408 | A1 | 5/2018 | |
| WO | 2019023222 | A1 | 1/2019 | |
| WO | 2019110556 | A1 | 6/2019 | |

OTHER PUBLICATIONS

Steinke et al., 1991, Cereal Chemistry 68, 7-12.
Johnston et al., Cereal Chemistry, 2004, 626-632, 81(5).

* cited by examiner

*Primary Examiner* — Lynn Y Fan
(74) *Attorney, Agent, or Firm* — David A. Fazzolare

(57) ABSTRACT

A method for increasing starch yield and/or gluten yield from corn kernels in a wet milling process, comprising contacting a fiber rich fraction of ground kernels, with an effective amount of $SO_2$, and an effective amount of one or more hydrolytic enzymes, wherein at least one of said hydrolytic enzymes is selected from xylanase and/or cellulase enzymes, during a fiber-washing step.

17 Claims, No Drawings

Specification includes a Sequence Listing.

SEQUENCE LISTING

```
<160> NUMBER OF SEQ ID NOS: 4

<210> SEQ ID NO 1
<211> LENGTH: 551
<212> TYPE: PRT
<213> ORGANISM: Artificial
<220> FEATURE:
<223> OTHER INFORMATION: Synthetic construct

<400> SEQUENCE: 1

Met Asp Glu Lys Asn Leu Leu Glu Asp Pro Asp Ser Asn Leu Ser Ala
1               5                   10                  15

Gly Ala Ser Ala Arg Ala Leu Ala Ala Thr Pro Met Leu His Val Gly
            20                  25                  30

Gly Arg Tyr Leu Lys Asp Pro Cys Asp Asn Asn Val Leu Leu His Gly
        35                  40                  45

Val Ala Ile Thr Pro Ser Pro Trp Phe Asn Gly Cys Gln Tyr Gly Ala
    50                  55                  60

Asn Ser Gly Tyr Cys Thr Trp Asp Asn Tyr Asn Val Gln Gly Cys Leu
65                  70                  75                  80

Asn Tyr Asn Lys Ala Val Met Asn Lys Leu Thr Ser Ala Ala Asp Gly
                85                  90                  95
```

-continued

```
Trp Tyr Leu Asn Tyr Ile Arg Leu His Ile Asp Pro Tyr Trp Thr Asn
            100                 105                 110

Asp Pro Gly Pro Ser Ile Pro Glu Asn Asp Ile Ser Arg Phe Asn Tyr
        115                 120                 125

Asn Arg Leu Val Thr Tyr Thr Asp Gln Val Ile Ile Pro Leu Ile Asn
    130                 135                 140

His Ala Arg Ser Arg Gly Met Tyr Val Ile Leu Arg Pro Pro Gly Val
145                 150                 155                 160

Cys Pro Asn Arg Ile Ala Val Asn Asp Ala Tyr His Ser Tyr Leu Lys
                165                 170                 175

Thr Val Trp Thr Phe Leu Ser Gln His Pro Gly Leu Lys Asn Ala Asp
            180                 185                 190

Asn Val Met Phe Glu Leu Ala Asn Glu Pro Val Glu Ile Leu Gly Thr
        195                 200                 205

Asn Gly Thr Trp Gly Gln Thr Gly Asn Glu His Phe Ala Ala Leu Lys
    210                 215                 220

Asn Phe Phe Gln Pro Leu Val Asn Ile Ile Arg Asn Asn Gly Ala Asn
225                 230                 235                 240

Asn Val Cys Trp Ile Pro Gly Thr Gly Trp Gln Ser His Tyr Gln Gly
                245                 250                 255

Tyr Pro Asn Asn Gln Ile Thr Gly Gly Asn Ile Gly Tyr Ala Val His
            260                 265                 270

Ile Tyr Pro Ser Tyr Trp Gly Gly Leu Ser Asn Tyr Gln Ala Phe Gln
        275                 280                 285

Asn Ala Trp Asn Ile Asn Val Lys Pro Ile Ala Asp Ile Ala Pro Ile
    290                 295                 300

Ala Ile Thr Glu Thr Asp Trp Ala Pro Gln Gly Tyr Gly Thr Phe Gly
305                 310                 315                 320

Ile Gly Thr Thr Gly Thr Ala Gly Gly Ser Gly Phe Gly Ala Asn Leu
                325                 330                 335

Lys Tyr Ile Val Asp Gln Ser Gly Asn Val Ser Trp Asn Val Leu Ala
            340                 345                 350

Pro Asp Asn Leu Leu His Lys Gly Asp Pro Asn Gly Gly Thr Ala Tyr
        355                 360                 365

Asn Asn Asp Trp Glu Ala Cys Ala Ala Pro Val Lys Gln Trp Phe Gln
    370                 375                 380

Gln Tyr Ala Lys Ser Asn Tyr Pro Val Gly Asn Cys Asn Thr Thr Ser
385                 390                 395                 400

Ser Leu Val Asn Asn Gly Ile Tyr Glu Ile Glu Phe Gln Thr Asp Ala
                405                 410                 415

Asn Lys Val Val Asp Leu Lys Ser Gly Glu Asp Ala Asn Gly Ala Val
            420                 425                 430

Leu Arg Pro Trp Thr Arg Asn Gly Ala Ala Ala Gln Arg Trp Val Ala
        435                 440                 445

Ile Asp Ala Gly Asn Gly Tyr Trp Arg Phe Val Ser Lys Ala Ser Ala
    450                 455                 460

Thr Asn Arg Cys Ile Thr Leu Ala Ser Asn Ser Asn Thr Leu Gly Thr
465                 470                 475                 480

Ser Ile Val Leu Trp Gln Asn Tyr Gly Asn Asp Ala Gln Ala Trp Gln
                485                 490                 495

Val Val Ala Val Ser Asn Gly Tyr Tyr Lys Ile Leu Ser Lys Val Asp
            500                 505                 510
```

```
Pro Thr Arg Gly Trp Asp Ile Pro Asn Cys Thr Met Asp Gly Asn Ser
        515                 520                 525

Asn Leu His Leu Trp Asp Tyr Tyr Gly Thr Ser Cys Gln Leu Phe Lys
    530                 535                 540

Phe Lys Tyr Ile Gly Met Asn
545                 550


<210> SEQ ID NO 2
<211> LENGTH: 405
<212> TYPE: PRT
<213> ORGANISM: Talaromyces leycettanus

<400> SEQUENCE: 2

Met Val His Leu Ser Ser Leu Ala Leu Ala Leu Ala Ala Gly Ser Gln
1               5                   10                  15

Leu Ala Gln Ala Ala Gly Leu Asn Thr Ala Ala Lys Ala Ile Gly Lys
            20                  25                  30

Leu Tyr Phe Gly Thr Ala Thr Asp Asn Pro Glu Leu Ser Asp Ser Thr
        35                  40                  45

Tyr Met Gln Glu Thr Asp Asn Thr Asp Asp Phe Gly Gln Leu Thr Pro
    50                  55                  60

Ala Asn Ser Met Lys Trp Asp Ala Thr Glu Pro Ser Gln Asn Thr Phe
65                  70                  75                  80

Thr Phe Thr Asn Gly Asp Gln Ile Ala Asn Leu Ala Lys Ser Asn Gly
                85                  90                  95

Gln Met Leu Arg Cys His Asn Leu Val Trp Tyr Asn Gln Leu Pro Ser
            100                 105                 110

Trp Val Thr Ser Gly Ser Trp Thr Asn Ala Thr Leu Leu Ala Ala Met
        115                 120                 125

Lys Asn His Ile Thr Asn Val Val Thr His Tyr Lys Gly Gln Cys Tyr
    130                 135                 140

Ala Trp Asp Val Val Asn Glu Ala Leu Asn Asp Asp Gly Thr Tyr Arg
145                 150                 155                 160

Ser Asn Val Phe Tyr Gln Tyr Ile Gly Glu Ala Tyr Ile Pro Ile Ala
                165                 170                 175

Phe Ala Thr Ala Ala Ala Ala Asp Pro Asn Ala Lys Leu Tyr Tyr Asn
            180                 185                 190

Asp Tyr Asn Ile Glu Tyr Pro Gly Ala Lys Ala Thr Ala Ala Gln Asn
        195                 200                 205

Ile Val Lys Met Val Lys Ala Tyr Gly Ala Lys Ile Asp Gly Val Gly
    210                 215                 220

Leu Gln Ser His Phe Ile Val Gly Ser Thr Pro Ser Gln Ser Ser Gln
225                 230                 235                 240

Gln Ser Asn Met Ala Ala Phe Thr Ala Leu Gly Val Glu Val Ala Ile
                245                 250                 255

Thr Glu Leu Asp Ile Arg Met Thr Leu Pro Ser Thr Ser Ala Leu Leu
            260                 265                 270

Ala Gln Gln Ser Thr Asp Tyr Gln Ser Thr Val Ser Ala Cys Val Asn
        275                 280                 285

Thr Pro Lys Cys Ile Gly Ile Thr Leu Trp Asp Trp Thr Asp Lys Tyr
    290                 295                 300

Ser Trp Val Pro Asn Thr Phe Ser Gly Gln Gly Asp Ala Cys Pro Trp
305                 310                 315                 320

Asp Ser Asn Tyr Gln Lys Lys Pro Ala Tyr Tyr Gly Ile Leu Thr Ala
                325                 330                 335
```

```
Leu Gly Gly Ser Ala Ser Thr Ser Thr Thr Thr Thr Leu Val Thr Ser
            340                 345                 350

Thr Arg Thr Ser Thr Thr Thr Ser Thr Ser Ala Thr Ser Thr Ser Thr
        355                 360                 365

Gly Val Ala Gln His Trp Gly Gln Cys Gly Gly Ile Gly Trp Thr Gly
    370                 375                 380

Pro Thr Thr Cys Ala Ser Pro Tyr Thr Cys Gln Glu Leu Asn Pro Tyr
385                 390                 395                 400

Tyr Tyr Gln Cys Leu
                405


<210> SEQ ID NO 3
<211> LENGTH: 325
<212> TYPE: PRT
<213> ORGANISM: Talaromyces pinophilus

<400> SEQUENCE: 3

Met His Phe Leu Ala Ala Leu Leu Ala Val Leu Pro Leu Val Ser Gly
1               5                   10                  15

Ser Pro Val Pro Glu Lys Arg Ser Gly Cys Ala Leu Pro Ser Thr Tyr
            20                  25                  30

Lys Trp Thr Ser Thr Gly Pro Leu Ala Ser Pro Lys Ser Gly Leu Val
        35                  40                  45

Ala Leu Arg Asp Tyr Ser His Val Ile Tyr Asn Gly Gln His Leu Val
    50                  55                  60

Tyr Gly Ser Thr Ala Asn Thr Ala Gly Ser Tyr Gly Ser Met Asn Phe
65                  70                  75                  80

Gly Leu Phe Ser Asp Trp Ser Glu Met Ser Ser Ala Ser Gln Asn Thr
                85                  90                  95

Met Ser Thr Gly Ala Val Ala Pro Thr Ile Phe Tyr Phe Ala Pro Lys
            100                 105                 110

Ser Val Trp Ile Leu Ala Tyr Gln Trp Gly Pro Tyr Ala Phe Ser Tyr
        115                 120                 125

Arg Thr Ser Thr Asp Pro Ser Asn Ala Asn Gly Trp Ser Ser Pro Gln
    130                 135                 140

Pro Leu Phe Thr Gly Thr Ile Ser Gly Ser Ser Thr Gly Val Ile Asp
145                 150                 155                 160

Gln Thr Val Ile Gly Asp Ser Glu Asn Met Tyr Leu Phe Phe Ala Gly
                165                 170                 175

Asp Asn Gly His Ile Tyr Arg Ala Ser Met Pro Ile Gly Asp Phe Pro
            180                 185                 190

Gly Ser Phe Gly Ser Ala Ser Thr Ile Val Leu Ser Asp Ser Thr Asn
        195                 200                 205

Asn Leu Phe Glu Ala Val Glu Val Tyr Thr Val Glu Gly Gln Asn Gln
    210                 215                 220

Tyr Leu Met Ile Val Glu Ala Ile Gly Ala Asn Gly Arg Tyr Phe Arg
225                 230                 235                 240

Ser Phe Thr Ala Ser Ser Leu Gly Gly Thr Trp Thr Ala Gln Ala Ser
                245                 250                 255

Thr Glu Ser Asn Pro Phe Ala Gly Lys Ala Asn Ser Gly Ala Thr Trp
            260                 265                 270

Thr Asn Asp Ile Ser Ser Gly Asp Leu Val Arg Thr Asn Pro Asp Gln
        275                 280                 285

Thr Gln Thr Ile Asp Ala Cys Asn Leu Gln Phe Leu Tyr Gln Gly Arg
```

```
    290                 295                 300

Ser Thr Ser Ser Gly Gly Asp Tyr Asn Leu Leu Pro Tyr Gln Pro Gly
305                 310                 315                 320

Leu Leu Thr Leu Ala
                325


<210> SEQ ID NO 4
<211> LENGTH: 319
<212> TYPE: PRT
<213> ORGANISM: Aspergillus niger

<400> SEQUENCE: 4

Met Val Gln Ile Lys Val Ala Ala Leu Ala Met Leu Phe Ala Ser Gln
1               5                   10                  15

Val Leu Ser Glu Pro Ile Glu Pro Arg Gln Ala Ser Val Ser Ile Asp
            20                  25                  30

Thr Lys Phe Lys Ala His Gly Lys Lys Tyr Leu Gly Asn Ile Gly Asp
        35                  40                  45

Gln Tyr Thr Leu Thr Lys Asn Ser Lys Thr Pro Ala Ile Ile Lys Ala
    50                  55                  60

Asp Phe Gly Ala Leu Thr Pro Glu Asn Ser Met Lys Trp Asp Ala Thr
65                  70                  75                  80

Glu Pro Ser Arg Gly Gln Phe Ser Phe Ser Gly Ser Asp Tyr Leu Val
                85                  90                  95

Asn Phe Ala Gln Ser Asn Asn Lys Leu Ile Arg Gly His Thr Leu Val
            100                 105                 110

Trp His Ser Gln Leu Pro Ser Trp Val Gln Ser Ile Thr Asp Lys Asn
        115                 120                 125

Thr Leu Ile Glu Val Met Glu Asn His Ile Thr Thr Val Met Gln His
    130                 135                 140

Tyr Lys Gly Lys Ile Tyr Ala Trp Asp Val Val Asn Glu Ile Phe Asn
145                 150                 155                 160

Glu Asp Gly Ser Leu Arg Asp Ser Val Phe Tyr Lys Val Ile Gly Glu
                165                 170                 175

Asp Tyr Val Arg Ile Ala Phe Glu Thr Ala Arg Ala Ala Asp Pro Asn
            180                 185                 190

Ala Lys Leu Tyr Ile Asn Asp Tyr Asn Leu Asp Ser Ala Ser Tyr Pro
        195                 200                 205

Lys Leu Thr Gly Met Val Ser His Val Lys Lys Trp Ile Ala Ala Gly
    210                 215                 220

Ile Pro Ile Asp Gly Ile Gly Ser Gln Thr His Leu Ser Ala Ala Leu
225                 230                 235                 240

Asn Ala Leu Ala Gly Ala Gly Thr Lys Glu Ile Ala Val Thr Glu Leu
                245                 250                 255

Asp Ile Ala Gly Ala Ser Ser Thr Asp Tyr Val Glu Val Val Glu Ala
            260                 265                 270

Cys Leu Asn Gln Pro Lys Cys Ile Gly Ile Thr Val Trp Gly Val Ala
        275                 280                 285

Asp Pro Asp Ser Trp Arg Ser Ser Ser Thr Pro Leu Leu Phe Asp Ser
    290                 295                 300

Asn Tyr Asn Pro Lys Pro Ala Tyr Thr Ala Ile Ala Asn Ala Leu
305                 310                 315
```

FIBER-WASHING IN CORN WET-MILLING

CROSS-REFERENCE TO RELATED APPLICATIONS

This application is a 35 U.S.C. 371 national application of international application no. PCT/CN2021/104908 filed Jul. 7, 2021, which claims priority or the benefit under 35 U.S.C. 119 of Chinese application no. PCT/C2020/101111 filed Jul. 9, 2020, the contents of which are fully incorporated herein by reference.

This application contains a Sequence Listing in computer readable form. The contents of the electronic sequence listing created on Jul. 5, 2021, named 15222-WO-PCT[2] SQ listing ST25.txt and 14 KB in size, is hereby incorporated by reference in its entirety.

FIELD OF THE INVENTION

The present invention relates to a method of improving/increasing starch and/or gluten yield from corn kernels in a wet milling process, by contacting said corn kernels with an enzyme composition comprising xylanases and/or cellulases, preferably during fiber washing.

BACKGROUND OF THE INVENTION

Conventional wet milling of corn is a process designed for the recovery and purification of starch and several coproducts including germ, gluten (protein) and fiber. Fiber is the least valuable coproduct, so the industry has put substantial effort into increasing the yield of the more valuable products, such as starch and gluten, while decreasing the fiber fraction. High quality starch is valuable as it can be used for a variety of commercial purposes after further processing to products such as dried starch, modified starch, dextrins, sweeteners and alcohol. Gluten is usually used for animal feed, as corn gluten meal (Around 60% protein) or corn gluten feed (Around 20% protein).

The wet milling process can vary significantly dependent on the specific mill equipment used, but usually the process include: grain cleaning, steeping, grinding, germ separation, a second grinding, fiber separation, gluten separation and starch separation. After cleaning the corn kernels, they are typically softened by soaking in water or in a dilute $SO_2$ solution under controlled conditions of time and temperature. Then, the kernels are grinded to break down the pericarp and the germ is separated from the rest of the kernel. The remaining slurry, mainly consisting of fiber, starch and gluten is finely ground and screened in a fiber washing process, to separate the fiber from starch and gluten, before the gluten and starch is separated and the starch can be purified in a washing/filtration process.

The use of enzymes in several steps of the wet milling process has been suggested, such as the use of enzymes for the steeping step of wet milling processes. The commercial enzyme product Steepzyme® (available from Novozymes A/S) has been shown suitable for the first step in wet milling processes, i.e., the steeping step where corn kernels are soaked in water.

More recently, "enzymatic milling", a modified wet milling process that uses proteases to significantly reduce the total processing time during corn wet milling and eliminates the need for sulfur dioxide as a processing agent, has been developed. Johnston et al., *Cereal Chem,* 81, p. 626-632 (2004).

U.S. Pat. No. 6,566,125 discloses a method for obtaining starch from maize involving soaking maize kernels in water to produce soaked maize kernels, grinding the soaked maize kernels to produce a ground maize slurry, and incubating the ground maize slurry with enzyme (e.g., protease).

U.S. Pat. No. 5,066,218 discloses a method of milling grain, especially corn, comprising cleaning the grain, steeping the grain in water to soften it, and then milling the grain with a cellulase enzyme.

WO 2002/000731 discloses a process of treating crop kernels, comprising soaking the kernels in water for 1-12 hours, wet milling the soaked kernels and treating the kernels with one or more enzymes including an acidic protease.

WO 2002/000911 discloses a process of starch gluten separation, comprising subjecting mill starch to an acidic protease.

WO 2002/002644 discloses a process of washing a starch slurry obtained from the starch gluten separation step of a milling process, comprising washing the starch slurry with an aqueous solution comprising an effective amount of acidic protease.

WO 2014/082566 and WO 2014/082564 disclose cellulolytic compositions for use in wet milling.

WO2016/095856 discloses compositions comprising xylanases and arabinofuranosidases and use of these copositions in fiber-wash in a corn wet-milling process.

WO2019/023222 discloses a wet-milling process applying GH5 xylanases and GH30 xylanases in combination with cellulases in the fiber-washing step.

WO2017/088820 discloses a process for improved starch release in corn wet-milling from fiber by adding an alpha-L-arabinofuranosidase (GH62) alone or in combination with a xylanase (GH10) in a fiberwash step.

WO2018/053220 discloses a fiber-washing system as part of a wet-milling process optimized for applying enzymes in the fiber-washing step by using a dedicated space/tank for the enzyme incubation.

While the art has investigated the effect of using enzymes in corn wet milling, during steeping/soaking of corn kernels, during grinding of the corn kernels, and in starch gluten separation, there is still a need for improved technology that may lower the energy expenditure and costs associated with corn wet milling and provide increased yield of starch and gluten.

SUMMARY OF THE INVENTION

In a first aspect the present invention relates to a method for increasing starch yield and/or gluten yield from corn kernels in a wet milling process, comprising contacting a fiber rich fraction of ground kernels, with an effective amount of $SO_2$, and an effective amount of one or more hydrolytic enzymes, wherein at least one of said hydrolytic enzymes is selected from xylanase and/or cellulase enzymes, during a fiber-washing step.

Definitions

Definition of Enzymes

Arabinofuranosidases/polypeptide with arabinofuranosidase activity: The term "arabinofuranosidase" means an alpha L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,2)- and/or (1,5)-linkages, arabinoxylans, and arabinogalactans. Alpha-L arabinofuranosidase is also known as arabinosidase, alpha-arabinosidase, alpha-L-arabinosidase, alphaarabinofuranosidase, polysaccharide alpha-L-arabinofuranosidase, alpha-L-arabinofuranoside hydrolase, L-arabinosidase, or alpha-L-arabinanase. Arabinofuranosidase activity can be determined using 5 mg of medium viscosity wheat arabinoxylan (Megazyme International Ireland, Ltd., Bray, Co. Wicklow, Ireland) per ml of 100 mM sodium acetate pH 5 in a total volume of 200 μl for 30 minutes at 40° C. followed by arabinose analysis by AMINEX® HPX-87H column chromatography (Bio-Rad Laboratories, Inc., Hercules, CA, USA). Arabinofuranosidases can be found in, e.g., the GH43, GH62, GH51 families according to Henrissat, 1991, A classification of glycosyl hydrolases based on amino-acid sequence similarities, *Biochem. J.* 280: 309-316, and Henrissat and Bairoch, 1996, Updating the sequence-based classification of glycosyl hydrolases, *Biochem. J.* 316: 695-696.

Beta-glucosidase/polypeptide with beta-glucosidase activity: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. Beta-glucosidase activity can be determined using p-nitrophenyl-beta-D-glucopyranoside as substrate according to the procedure of Venturi et al., 2002, *J. Basic Microbiol.* 42: 55-66. One unit of beta-glucosidase is defined as 1.0 μmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Beta-xylosidase/polypeptide with beta-xylosidase activity: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. Beta-xylosidase activity can be determined using 1 mM p-nitrophenyl-beta-D-xyloside as substrate in 100 mM sodium citrate containing 0.01% TWEEN® 20 at pH 5, 40° C. One unit of beta-xylosidase is defined as 1.0 μmole of p-nitrophenolate anion produced per minute at 40° C., pH 5 from 1 mM p-nitrophenyl-beta-D-xyloside in 100 mM sodium citrate containing 0.01% TWEEN® 20.

Cellobiohydrolase/polypeptide with cellobiohydrolase activity: The term "cellobiohydrolase" means a 1,4-beta-D-glucan cellobiohydrolase (E.C. 3.2.1.91 and E.C. 3.2.1.176) that catalyzes the hydrolysis of 1,4-beta-D-glucosidic linkages in cellulose, cellooligosaccharides, or any beta-1,4-linked glucose containing polymer, releasing cellobiose from the reducing end (cellobiohydrolase I) or non-reducing end (cellobiohydrolase II) of the chain (Teeri, 1997, *Trends in Biotechnology* 15: 160-167; Teeri et al., 1998, *Biochem. Soc. Trans.* 26: 173-178). Cellobiohydrolase activity can be determined according to the procedures described by Lever et al., 1972, *Anal. Biochem.* 47: 273-279; van Tilbeurgh et al., 1982, *FEBS Letters* 149: 152-156; van Tilbeurgh and Claeyssens, 1985, *FEBS Letters* 187: 283-288; and Tomme et al., 1988, *Eur. J. Biochem.* 170: 575-581.

Cellulolytic enzyme or cellulase/polypeptide with cellulase activity or cellulolytic activity: The term "cellulolytic enzyme" or "cellulase" means one or more (e.g., several) enzymes that hydrolyze a cellulosic material, which comprise any material comprising cellulose, such as fiber. Cellulytic enzymes include endoglucanase(s) (E.C 3.2.1.4), cellobiohydrolase(s) (E.C 3.2.1.91 and E.C 3.2.1.150), beta-glucosidase(s) (E.C. 3.2.1.21), or combinations thereof. The two basic approaches for measuring cellulolytic enzyme activity include: (1) measuring the total cellulolytic enzyme activity, and (2) measuring the individual cellulolytic enzyme activities (endoglucanases, cellobiohydrolases, and beta-glucosidases) as reviewed in Zhang et al., 2006, *Biotechnology Advances* 24: 452-481. Total cellulolytic enzyme activity can be measured using insoluble substrates, including Whatman No 1 filter paper, microcrystalline cellulose, bacterial cellulose, algal cellulose, cotton, pretreated lignocellulose, etc. The most common total cellulolytic activity assay is the filter paper assay using Whatman No 1 filter paper as the substrate. The assay was established by the International Union of Pure and Applied Chemistry (IUPAC) (Ghose, 1987, *Pure Appl. Chem.* 59: 257-68).

Cellulolytic enzyme activity can be determined by measuring the increase in production/release of sugars during hydrolysis of a cellulosic material by cellulolytic enzyme(s) under the following conditions: 1-50 mg of cellulolytic enzyme protein/g of cellulose in pretreated corn stover (PCS) (or other pretreated cellulosic material) for 3-7 days at a suitable temperature such as 40° C.-80° C., e.g., 40° C., 45° C., 50° C., 55° C., 60° C., 65° C., 70° C., 75° C., or 80° C., and a suitable pH, such as 4-9, e.g., 4.0, 4.5, 5.0, 5.5, 6.0, 6.5, 7.0, 7.5, 8.0, 8.5, or 9.0, compared to a control hydrolysis without addition of cellulolytic enzyme protein. Typical conditions are 1 ml reactions, washed or unwashed PCS, 5% insoluble solids (dry weight), 50 mM sodium acetate pH 5, 1 mM $MnSO_4$, 50° C., 55° C., or 60° C., 72 hours, sugar analysis by AMINEX® HPX-87H column chromatography (Bio-Rad Laboratories, Inc., Hercules, CA, USA).

Endoglucanase: The term "endoglucanase" means an endo-1,4-(1,3; 1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

Family 61 glycoside hydrolase: The term "Family 61 glycoside hydrolase" or "Family GH61" or "GH61" means a polypeptide falling into the glycoside hydrolase Family 61 according to Henrissat, 1991, A classification of glycosyl hydrolases based on amino-acid sequence similarities, *Biochem. J.* 280: 309-316, and Henrissat and Bairoch, 1996, Updating the sequence-based classification of glycosyl hydrolases, *Biochem. J.* 316: 695-696. The enzymes in this family were originally classified as a glycoside hydrolase family based on measurement of very weak endo-1,4-beta-D-glucanase activity in one family member. The structure and mode of action of these enzymes are non-canonical and they cannot be considered as bona fide glycosidases. However, they are kept in the CAZy classification on the basis of their capacity to enhance the breakdown of lignocellulose when used in conjunction with a cellulase or a mixture of cellulases. The GH61 polypeptides have recently been classified as lytic polysaccharide monooxygenases (Quinlan et al., 2011, *Proc. Natl. Acad. Sci. USA* 208: 15079-15084; Phillips et al., 2011, *ACS Chem. Biol.* 6: 1399-1406; Lin et al., 2012, *Structure* 20: 1051-1061) and are designated "Auxiliary Activity 9" or "AA9" polypeptides.

Hydrolytic enzymes or hydrolase/polypeptide with hydrolase activity: "Hydrolytic enzymes" refers to any catalytic protein that use water to break down substrates. Hydrolytic enzymes include cellulases (EC 3.2.1.4), xylanases (EC 3.2.1.8) arabinofuranosidases (EC 3.2.1.55 (Non-reducing end alpha-L-arabinofuranosidases); EC 3.2.1.185 (Non-reducing end beta-L-arabinofuranosidases) cellobiohydrolase I (EC 3.2.1.150), cellobiohydrolase II (E.C. 3.2.1.91), cellobiosidase (E.C. 3.2.1.176), beta-glucosidase (E.C. 3.2.1.21), beta-xylosidases (EC 3.2.1.37).

Xylanases/polypeptide with xylanase activity: The term "xylanase" means a 1,4-beta-D-xylan-xylohydrolase (E.C. 3.2.1.8) that catalyzes the endohydrolysis of 1,4-beta-D-xylosidic linkages in xylans. Xylanase activity can be determined with 0.2% AZCL-arabinoxylan as substrate in 0.01% TRITON® X-100 and 200 mM sodium phosphate pH 6 at 37° C. One unit of xylanase activity is defined as 1.0 μmole of azurine produced per minute at 37° C., pH 6 from 0.2% AZCL-arabinoxylan as substrate in 200 mM sodium phosphate pH 6. Xylanases can be found in, e.g., the GH5, GH30, GH10, and GH11 families.

GH5 polypeptide: refers to a polypeptide with enzyme activity, the polypeptide being classified as member of the Glycoside hydrolase family 5 in the database of Carbohydrate-Active EnZymes (CAZymes) (http://www.cazv.org/).

GH8 polypeptide: refers to a polypeptide with enzyme activity, the polypeptide being classified as member of the Glycoside hydrolase family 5 in the database of Carbohydrate-Active EnZymes (CAZymes) (http://www.cazy.org/).

GH30 polypeptide: refers to a polypeptide with enzyme activity, the polypeptide being classified as member of the Glycoside hydrolase family 30 in the database of Carbohydrate-Active EnZymes (CAZymes) (http://www.cazy.org/).

GH10 polypeptide: refers to a polypeptide with enzyme activity, the polypeptide being classified as member of the Glycoside hydrolase family 10 in the database of Carbohydrate-Active EnZymes (CAZymes) available at http://www.cazy.org/. (Lombard, V.; Golaconda Ramulu, H.; Drula, E.; Coutinho, P. M.; Henrissat, B. (21 Nov. 2013). "The carbohydrate-active enzymes database (CAZy) in 2013". Nucleic Acids Research. 42 (D1): D490-D495; Cantarel BL, Coutinho PM, Rancurel C, Bernard T, Lombard V, Henrissat B (January 2009). "The Carbohydrate-Active EnZymes database (CAZy): an expert resource for Glycogenomics". Nucleic Acids Res. 37 (Database issue): D233-8).

GH11 polypeptide refers to a polypeptide with enzyme activity, the polypeptide being classified as member of the Glycoside hydrolase family 11 in the database of Carbohydrate-Active EnZymes (CAZymes).

GH62 polypeptide: refers to a polypeptide with enzyme activity, the polypeptide being classified as member of the Glycoside hydrolase family 62 in the database of Carbohydrate-Active EnZymes (CAZymes).

GH43 polypeptide: refers to a polypeptide with enzyme activity, the polypeptide being classified as member of the Glycoside hydrolase family 43 in the database of Carbohydrate-Active EnZymes (CAZymes).

GH51 polypeptide: refers to a polypeptide with enzyme activity, the polypeptide being classified as member of the Glycoside hydrolase family 51 in the database of Carbohydrate-Active EnZymes (CAZymes).

Other Definitions

In the present context, terms are used in manner being ordinary to a skilled person. Some of these terms are elucidated below:

Contact time: For one or more enzymes to react with a substrate, the one or more enzymes have to be in contact with the substrate. "Contact time" refers to the time period in which an effective amount of one or more enzymes is in contact with at least a fraction of a substrate mass. The enzymes may not be in contact with all of the substrate mass during the contact time, however mixing the one or more enzymes with a substrate mass allows the potential of enzymatically catalyzed hydrolysis of a fraction of the substrate mass during the contact time.

Corn kernel: A variety of corn kernels are known, including, e.g., dent corn, flint corn, pod corn, striped maize, sweet corn, waxy corn and the like.

Some corn kernels has an outer covering referred to as the "Pericarp" that protects the germ in the kernels. It resists water and water vapour and is undesirable to insects and microorganisms. The only area of the kernels not covered by the "Pericarp" is the "Tip Cap", which is the attachment point of the kernel to the cob.

Corn kernels or a fraction of the corn kernels: This term is used to describe the corn kernels through the process of wet milling. When the corn kernels are broken down and processed, all fractionated parts of the corn kernel are considered to be included when this term is used. The term include for example: soaked kernels, grinded kernels, corn kernel mass, a first fraction, a second fraction, one or more fractions of the corn kernel mass ect.

Corn kernel mass: is preferably used to reference a mass comprising fiber, gluten and starch, preferably achieved by steaming and grinding crop kernels and separating a mass comprising fiber, gluten and starch from germs. As the corn kernel mass move through the fiber washing, it is separated into several fractions, including a first fraction (s) and a second fraction (f). Hence, "fractions of corn kernel mass" and "one or more fractions of corn kernel mass" refer inter alia to these first (s) and second fractions (f).

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide having one or more (e.g., several) amino acids absent from the amino and/or carboxyl terminus of a mature polypeptide, wherein the fragment has pectin lyase activity.

Germ: The "Germ" is the only living part of the corn kernel. It contains the essential genetic information, enzymes, vitamins, and minerals for the kernel to grow into a corn plant. In yellow dent corn, about 25 percent of the germ is corn oil. The endosperm covered or surrounded by the germ comprises about 82 percent of the kernel dry weight and is the source of energy (starch) and protein for the germinating seed. There are two types of endosperm, soft and hard. In the hard endosperm, starch is packed tightly together. In the soft endosperm, the starch is loose.

Gluten: Gluten is a protein, made up from two smaller proteins, glutenin and gliadin. Herein "gluten" refers to the majority of proteins found in corn kernels. The major products of gluten from corn wet milling is corn gluten meal (Approximately 60% protein) and corn gluten feed (Approximately 20% protein).

Grind or grinding: The term "grinding" refers to breaking down the corn kernels into smaller components.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Incubation time: Time in which the one or more fractions of the corn kernel mass is in contact with hydrolytic enzyme during fiber washing, without being screened.

In many preferred embodiments, a method according to the present invention utilises a system comprising a space (V), or "incubator", inside which the material is "left to be affected" by the enzymes and in such situations, the incubation time may be determined by:

$$t_{it} = \frac{\text{volume of incubator } [\text{m}^3] * \text{density of inflow to incubator } [\text{kg/m}^3]}{\text{mass inflow per time unit to the incubator } [\text{kg/s}]}$$

Alternatively, if the inflow to the incubator is expressed in terms of volume per time unit:

$$t_{it} = \frac{\text{volume of incubator } [\text{m}^3]}{\text{volume inflow per time unit to the incubator } [\text{m}^3/\text{s}]}$$

Mature polypeptide: The term "mature polypeptide" means a polypeptide in its final form following translation and any post-translational modifications, such as N-terminal processing, C-terminal truncation, glycosylation, phosphorylation, etc. It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide.

Mill equipment: "Mill equipment" refers to all equipment used on a mill. The wet milling process will vary dependent on the available mill equipment. Examples of mill equipment can be steeping tanks, evaporator, screw press, rotatory dryer, dewatering screen, centrifuge, hydrocyclone ect. The size, and number of each mill equipment/milling lines can vary on different mills, which will affect the milling process. For example, the number of fiber washing screen units can vary and so can the size of a centrifuge.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Retention time: The time in which one or more hydrolytic enzymes and corn kernels or a fraction of the corn kernels are allowed to react during the fiber washing procedure.

In some embodiments, the retention time is the time period in which the corn kernel mass, received in the first screen unit (S1) and one or more fractions thereof, are contacted with an effective amount of one or more hydrolytic enzymes before leaving the fiber washing system again. During the retention time, the one or more fractions of corn kernel mass is incubated with one or more hydrolytic enzymes in a space (V), before it leaves the fiber washing system, as part of a first fraction (s1) from the most upstream screen unit (S1) or as part of a second fraction (f4) from the most downstream screen unit (S4).

Retention time may preferably be estimated as the average duration of time solid matter spends in a fiber washing system as defined in relation to the present invention. This may be estimated by the following relation:

$$t_{rt} = \frac{\text{volume of system: } [\text{m}^3] * \text{density of mass inflow } [\text{kg/m}^3]}{\text{mass inflow per time unit to the system } [\text{kg/s}]}$$

Alternatively, if the inflow to the system is expressed in terms of volume per time unit:

$$t_{it} = \frac{\text{volume of system } [m^3]}{\text{volume inflow per time unit to the system } [m^3/s]}$$

The volume of the system is typically set equal to the sum of the volumes of all voids in the system; however, as the tubing in the system typically is made small, it may be preferred to disregard the volume of the tubing.

Screened: The term "screened" or "screening" refers to the process of separating corn kernel mass into a first fraction s and a second fraction f and movement of these fractions from one screen unit to another. A non-screening period is a non-separating period provided for incubation of corn kernel mass or fractions thereof with enzymes.

Sequence identity: The relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. Version 6.1.0 was used.

The optional parameters used are gap open penalty of 10, gap extension penalty of 0.5, and the EBLOSUM62 (EMBOSS version of BLOSUM62) substitution matrix. The output of Needle labelled "longest identity" (obtained using the –nobrief option) is used as the percent identity and is calculated as follows: (Identical Residues×100)/(Length of Alignment–Total Number of Gaps in Alignment).

Starch: The term "starch" means any material comprised of complex polysaccharides of plants, composed of glucose units that occurs widely in plant tissues in the form of storage granules, consisting of amylose and amylopectin, and represented as $(C_6H_{10}O_5)n$, where n is any number.

Steeping or soaking: The term "steeping" means soaking the crop kernel with water and optionally $SO_2$.

DETAILED DESCRIPTION

It is an object of the present invention to provide a method that improves starch and gluten yield from a corn wet milling process.

Particularly, it is an object of the present invention to provide a method for improving the starch and/or gluten yields that can be obtained from corn kernels in a wet milling process, by treating the fiber fraction with a hydrolytic enzyme composition, preferably during a fiber washing procedure. The inventors of the present invention has surprisingly found that the enzymatic treatment of corn fiber in the presence of at least a xylanase and/or cellulase and an effective amount of $SO_2$, increases the release of bound starch and gluten from fiber and thus improve the starch and/or gluten yields that can be obtained.

The Wet Milling Process:

Corn kernels are wet milled in order to open up the kernels and separate the kernels into its four main constituents: starch, germ, fiber and gluten.

The wet milling process can vary significantly from mill to mill, however conventional wet milling usually comprises the following steps:

1. Steeping
2. Grinding
3. Separation into streams comprising:
   i) germ; ii) fiber, iii) starch and gluten
4. Fiber washing, pressing and drying
5. Starch/gluten separation, and
6. Starch washing.

Steeping, Grinding and Germ Separation

Corn kernels are softened by soaking in water for between about 30 minutes to about 48 hours, preferably 30 minutes to about 15 hours, such as about 1 hour to about 6 hours at a temperature of about 50° C., such as between about 45° C. to 60° C. During steeping, the kernels absorb water, increasing their moisture levels from 15 percent to 45 percent and more than doubling in size. The optional addition of e.g. 0.1 percent sulphur dioxide ($SO_2$) and/or $NaHSO_3$ to the water prevents excessive bacteria growth in the warm environment. As the corn swells and softens, the mild acidity of the steep water begins to loosen the gluten bonds within the corn and release the starch. After the corn kernels are steeped they are cracked open by grinding to release the germ. The germ contains corn oil. The germ is separated from the heavier density mixture of starch, gluten and fiber (corn kernel mass comprising fiber, starch and gluten) essentially by "floating" the germ segment free of the other substances under closely controlled conditions. This method serves to eliminate any adverse effect of traces of corn oil in later processing steps. Subsequently the germ may be dried and oil extracted.

The corn kernel mass comprising fiber, starch and gluten are subsequently separated into fiber, starch, and gluten fractions, e.g., in a fiber-washing step.

Fiber Washing, Pressing and Drying

To get maximum starch and gluten recovery, while keeping any fiber in the final product to an absolute minimum, it is necessary to wash the free starch and gluten from the fiber during processing. The free starch and gluten is separated from fiber during screening (washing) and collected as mill starch. The remaining fiber is then pressed to decrease the water content.

Starch Gluten Separation

The starch-gluten suspension as well as additional starch gluten released from the fiber-washing step, called mill starch, is separated into starch and gluten. Gluten has a low density compared to starch. By passing mill starch through a centrifuge, the gluten is readily spun out.

Starch Washing

The starch slurry from the starch separation step contains some insoluble protein and much of solubles. They have to be removed before a top quality starch (high purity starch) can be made. The starch, with just one or two percent protein remaining, is diluted, washed 8 to 14 times, re-diluted and washed again in hydro-clones to remove the last trace of protein and produce high quality starch, typically more than 99.5% pure.

Products of wet milling: Wet milling can be used to produce, without limitation, corn steep liquor, corn gluten feed, germ, corn oil, corn gluten meal, corn starch, modified corn starch, syrups such as corn syrup, and corn ethanol.

An aspect of the present disclosure is to provide a method to increase the total starch yield and/or gluten yield that can be obtained from corn kernels in a wet milling process, the method comprising: Admixing corn kernels or a fraction of the corn kernels with an enzyme composition comprising an effective amount of one or more hydrolytic enzymes, wherein at least one of said hydrolytic enzymes is selected from the group consisting of a xylanase polypeptide, and/or cellulase polypeptide or a combination thereof.

Some of the starch and/or gluten in corn kernels or fractions of corn kernels, may be bound to the fiber fraction and never released during the wet milling process. However, addition of hydrolytic enzymes, which may include any catalytic protein that can use water to break down substrates present in corn kernels, may release some of the bound starch and/or gluten and thus increase the total yield of starch and/or gluten in the wet milling process.

The present inventors have surprisingly found that the effect of adding hydrolytic enzymes, such as cellulases and xylanases, to the fiber rich fraction of the ground kernel mass, particularly in a fiber-washing step can be boosted at elevated levels of $SO_2$.

In a first aspect the present invention therefore relates to a method for increasing starch yield and/or gluten yield from corn kernels in a wet milling process, the method comprising contacting ground corn kernels or a fraction of the ground kernels, particularly a fiber rich fraction, with an effective amount of $SO_2$, and an effective amount of one or more hydrolytic enzymes, wherein at least one of said hydrolytic enzymes is selected from xylanase and/or cellulase enzymes. Preferably, the contact is performed during a fiber-washing step.

In one embodiment, the method of the present invention leads to an increase in the amount of starch and/or gluten released from fiber during the wet milling process compared to a process where no $SO_2$ is present/added.

The specific procedure and the equipment used in the wet milling process can vary, but the main principles of the process remains the same (see description on wet milling process).

In one particular embodiment, the method of the invention comprise the steps of:

a) soaking the corn kernels in water to produce soaked kernels;
b) grinding the soaked kernels to produce ground kernels;
c) separating germs from the ground kernels to produce a corn kernel mass comprising fiber, starch and gluten; and
d) subjecting the resultant corn kernel mass comprising fiber to a fiber washing procedure, thereby separating starch, gluten, and fiber;

wherein at least a xylanase and/or cellulase and an effective amount of $SO_2$ is present/added before or during step d).

To get maximum starch and gluten recovery, while keeping any fiber in the final product to an absolute minimum, it is necessary to wash the free starch and gluten from the fiber fraction during processing. The fiber is collected, slurried and screened, typically after soaking, grinding and separation of germs from the corn kernels, to reclaim any residual starch or gluten in the corn kernel mass. This process is herein referred to as the fiber washing procedure.

In a preferred embodiment, said corn kernels or a fiber rich fraction of said corn kernels is admixed with said one or more hydrolytic enzymes during the step of subjecting the corn kernel mass to a fiber washing procedure.

According to the invention, in order to maximize the effect of the hydrolytic enzymes during the fiber washing step, a boosting effect is observed when an effective amount of $SO_2$ is present during the fiber wash. $SO_2$ is often added in the step of soaking the kernels, however, in the downstream steps, such as in the fiber-washing step, $SO_2$ levels will have dropped below the levels claimed according to the present method.

In one embodiment $SO_2$ is present/added during fiber wash in amounts of at least 400 ppm, at least 450 ppm, at least 500 ppm, at least 600 ppm, at least 700 ppm, at least 800 ppm.

In another embodiment SO2 is present/added during fiber wash in amounts in a range from 400-3000 ppm, 500-2000 ppm, 600-1500 ppm, such as 600-1200 ppm.

The specific equipment used in the fiber washing procedure may vary, but the main principle of the process remains the same. WO2018/053220 describes a fiber-washing system including a dedicated enzyme incubation space/tank. Based on this disclosure and the general knowledge of the skilled person it will be possible to design a fiber-washing system resulting in sufficient incubation time for the hydrolytic enzymes to work. In one embodiment, said corn kernels or a fraction of said corn kernels, e.g., a fiber rich fraction, is allowed to react with said one or more hydrolytic enzymes for at least 15 minutes, such as at least 20 minutes, at least 25 minutes, at least 30 minutes, at least 35 minutes, at least 40 minutes, at least 45 minutes, at least 50 minutes, at least 55 minutes, at least 60 minutes, at least 70 minutes, at least 80 minutes, at least 90 minutes, at least 100 minutes, at least 110 minutes or at least 120 minutes.

In one embodiment, said fiber washing procedure comprise the use of a fiber washing system optimized for introduction of one or more hydrolytic enzymes, wherein the fiber washing system comprise a space (V) configured to provide a total reaction time in the fiber washing system (retention time) of at least 35 minutes, such as at least 40 minutes, at least 45 minutes, at least 50 minutes, at least 60 minutes, at least 70 minutes, at least 80 minutes, at least 90 minutes, at least 100 minutes, at least 110 minutes or at least 120 minutes and less than 48 hours, such as less than 40 hours, less than 36 hours, less than 30 hours, less than 24 hours, less than 20 hours, less than 12 hours, less than 10 hours, less than 8 hours, less than 6 hours, less than 5 hours, less than 4 hours, less than 3 hours. In one embodiment the total retention time in the fiber washing system is between 35 minutes and 48 hours such as between 35 minutes and 24 hours, 35 minutes and 12 hours, 35 minutes and 6 hours, 35 minutes and 5 hours, 35 minutes and 4 hours, 35 minutes and 3 hours, 35 minutes and 2 hours, 45 minutes and 48 hours, 45 minutes and 24 hours, 45 minutes and hours, 45 minutes and 6 hours, 45 minutes and 5 hours, 45 minutes and 4 hours, 45 minutes and 3 hours, 45 minutes and 2 hours 1-48 hours, 1-24 hours, 1-12 hours, 1-6 hours, 1-5 hours, 1-4 hours, 1-3 hours, 1-2 hours.

In one embodiment, the fiber washing system comprises:

a plurality of screen units (S1 . . . S4) being fluidly connected in a counter current washing configuration; each screen unit being configured for separating a stream of corn kernel mass and liquid into two fractions: a first fraction (s) and a second fraction (f), said second fraction (f) containing a higher amount measured in wt % fiber than the first fraction (s);

a space (V) arranged in the system and being fluidly connected to receive said first fraction (s), said second fraction (f), or a mixed first and second fraction (s,f), preferably only a second fraction (f), and configured to provide an incubation time for one or both fractions received in the space; and outletting the thereby incubated one or both fractions to a downstream screen unit (S4), wherein the system is configured for
inletting corn kernel mass and liquid to the most upstream screen unit (S1)
outletting the first fraction (s1) from the most upstream screen unit (S1) as a product stream containing starch,
inletting process water, preferably arranged for inletting process water to a most downstream screen unit (S4),
outletting the second fraction (f4) from most downstream screen unit (S4) as a washed corn kernel mass containing a lower amount of starch and gluten than the original corn kernel mass.
introducing hydrolytic enzymes into the system.

In one embodiment, the incubation time in said space (V) configured into the fiber washing system is at least 5 minutes such as at least 10 minutes, at least 15 minutes, at least 20 minutes, at least 30 minutes, at least 40 minutes, at least 45 minutes, at least 50 minutes, at least 60 minutes, at least 70 minutes, at least 80 minutes, at least 90 minutes, at least 100 minutes, at least 110 minutes or at least 120 minutes and less than 48 hours, such as less than 40 hours, less than 36 hours, less than 30 hours, less than 24 hours, less than 20 hours, less than 12 hours, less than 10 hours, less than 8 hours, less than 6 hours, less than 5 hours, less than 4 hours, less than 3 hours.

In one embodiment the incubation time in said space (V) is between 35 minutes and 48 hours such as between 35 minutes and 24 hours, 35 minutes and hours, 35 minutes and 6 hours, 35 minutes and 5 hours, 35 minutes and 4 hours, 35 minutes and 3 hours, 35 minutes and 2 hours, 45 minutes and 48 hours, 45 minutes and 24 hours, 45 minutes and 12 hours, 45 minutes and 6 hours, 45 minutes and 5 hours, 45 minutes and 4 hours, 45 minutes and 3 hours, 45 minutes and 2 hours 1-48 hours, 1-24 hours, 1-12 hours, 1-6 hours, 1-5 hours, 1-4 hours, 1-3 hours, 1-2 hours.

In one embodiment, the incubation temperature in said space (V) is between 25 and 95° C., such as between 25 and 90° C., 25 and 85° C., 25 and 80° C., 25 and 75° C., 25 and 70° C., 25 and 65° C., 25 and 60° C., 25 and 55° C., 25 and 53° C., 25 and 52° C., 30 and 90° C., 30 and 85° C., 30 and 80° C., 30 and 75° C., 30 and 70° C., 30 and 65° C., 30 and 60° C., 30 and 55° C., 30 and 53° C., 30 and 52° C., 35 and 90° C., 35 and 85° C., 35 and 80° C., 35 and 75° C., 35 and 70° C., 35 and 65° C., 35 and 60° C., 35 and 55° C., 35 and 53° C., 35 and 52° C., 39 and 90° C., 39 and 85° C., 39 and 80° C., 39 and 75° C., 39 and 70° C., 39 and 65° C., 39 and 60° C., 39 and 55° C., 39 and 53° C., 39 and 52° C., such as 46 and 52° C.

Further, the dimension of the space (in $m^3$) is preferably configured to provide an incubation time of at least at least 5 minutes, such as at least 10 minutes, at least 15 minutes, at least 20 minutes at least 25 minutes, at least 30 minutes, at least 35 minutes, at least 40 minutes, at least 45 minutes, at least 50 minutes, at least 55 minutes, at least 60 minutes, at least 70 minutes, at least 80 minutes, at least 90 minutes, at least 100 minutes, at least 110 minutes, at least 120 minutes.

The space (V) designated for incubation preferably has a volume of at least 30 $m^3$, at least 40 $m^3$, at least 50 $m^3$, at least 60 $m^3$, at least 70, $m^3$, at least 80, $m^3$, at least 90, $m^3$, at least 100 $m^3$, at least 110 $m^3$, at least 120 $m^3$, at least 130 $m^3$, at least 140 $m^3$, at least 150 $m^3$, at least 160 $m^3$, at least 170 $m^3$, at least 180 $m^3$, at least 190 $m^3$, at least 200 $m^3$, at least 210 $m^3$, at least 220 $m^3$, at least 230 $m^3$, at least 240 $m^3$, at least 250 $m^3$, at least 260 $m^3$, at least 270 $m^3$, at least 280 $m^3$, at least 290 $m^3$, at least 300 $m^3$, at least 400 $m^3$, or at least 500 $m^3$. The incubation time may also be in more than one space V with a total or combined volume of at least 100 $m^3$, at least 110 $m^3$, at least 120 $m^3$, at least 130 $m^3$, at least 140 $m^3$, at least 150 $m^3$, at least 160 $m^3$, at least 170 $m^3$, at least 180 $m^3$, at least 190 $m^3$, at least 200 $m^3$, at least 210 $m^3$, at least 220 $m^3$, at least 230 $m^3$, at least 240 $m^3$, at least 250 $m^3$, at least 260 $m^3$, at least 270 $m^3$, at least 280 $m^3$, at least 290 $m^3$, at least 300 $m^3$, at least 400 $m^3$, at least 500 $m^3$.

During the incubation time, it is preferred that the fluid received in the space V is not screened. Thus, the fluid leaving the space V has the same composition, e.g. of starch and fiber, as the fluid received in the space V, although it preferably contains a higher proportion of starch that has been released from the fibers.

To assure intimate contact between the enzymes and the fiber, it may be preferred to configure the space V for agitation of matter contained in said space V, such as by comprising a rotor or impeller.

It is preferred to arrange the space V downstream of the most upstream screen unit S1 and upstream of said most downstream screen unit S4; in particular, the space V is arranged to feed fluid into the second most downstream screen unit S3.

Hydrolytic Enzymes Suitable for the Method of the Invention

In one embodiment, hydrolytic enzymes suitable for use in the method of the invention comprise one or more enzymes selected form the group consisting of: cellulases (EC 3.2.1.4), xylanases (EC 3.2.1.8) arabinofuranosidases (EC 3.2.1.55 (Non-reducing end alpha-L-arabinofuranosidases); EC 3.2.1.185 (Non-reducing end beta-L-arabinofuranosidases) cellobiohydrolase I (EC 3.2.1.150), cellobiohydrolase II (E.C. 3.2.1.91), cellobiosidase (E.C. 3.2.1.176), beta-glucosidase (E.C. 3.2.1.21), beta-xylosidases (EC 3.2.1.37) and proteases (E.C 3.4).

In one embodiment the xylanase is selected from the group consisting of a GH5 polypeptide, GH30 polypeptide, a GH10 polypeptide, a GH11 polypeptide, a GH8 polypeptide or a combination thereof.

In another embodiment the hydrolytic enzymes comprise one or more cellulases. The cellulases may be selected from at least the group consisting of an endoglucanase (EG), and a cellobiohydrolase (CBH). More particularly, the cellulase (s) comprise(s) one or more enzymes selected from the group consisting of an endoglucanase, a cellobiohydrolase I, a cellobiohydrolase II, or a combination thereof.

In one embodiment the hydrolytic enzymes further comprise an arabinofuranosidase. The arabinofuranosidase may be selected from the group consisting of a GH43 polypeptide, a GH62 polypeptide, GH51 polypeptide. Particularly a GH62 polypeptide.

In one embodiment, the one or more hydrolytic enzymes is expressed in an organism with a cellulase background, such as *Trichoderma reesei*. According to these embodiments the xylanase and or arabinofuranosidase polypeptides defined according to the invention is/are expressed together with endogenous cellulases from *Trichoderma.*

In one embodiment, the enzyme composition comprising one or more hydrolytic enzymes may comprise cellulases expressed in *Trichoderma reesei* and other hydrolotic enzymes which are added to the enzyme composition in a purified or semi-purified form.

In one embodiment, the one or more hydrolytic enzymes are purified. The purified enzymes may be used in an enzyme composition as described in other embodiments of the present invention.

In one embodiment, the one or more hydrolytic enzymes is/are in a liquid composition. The composition may be homogenous or heterogeneous.

In one embodiment, the one or more hydrolytic enzymes is/are in a solid composition.

In one embodiment, the effective amount of one or more hydrolytic enzymes admixed with one or more fractions of said corn kernel mass, is between 0.005-0.5 kg enzyme protein (EP)/metric tonne (MT) corn kernels entering the wet milling process, such as between 0.010-0.5 kg EP/MT corn kernel, such as between 0.05-0.5 kg/MT corn kernel or 0.075-0.5 kg/MT or 0.1-0.5 kg/MT corn kernel or 0.005-0.4 kg/MT corn kernel or 0.01-0.4 kg/MT corn kernel or 0.05-0.4 kg/MT corn kernel or 0.075-0.4 kg/MT corn kernel or 0.1-0.4 kg/MT corn kernel or 0.005-0.3 kg/MT corn kernel or 0.01-0.3 kg/MT corn kernel or 0.05-0.3 kg/MT corn kernel or 0.075-0.3 kg/MT or 0.1-0.3 kg/MT corn kernel or 0.005-0.2 kg/MT corn kernel or 0.010-0.2 kg/MT corn kernel or 0.05-0.2 kg/MT corn kernel or 0.075-0.2 kg/MT or 0.1-0.2 kg/MT corn kernel or such as 0.075-0.10 kg/MT corn kernel or 0.075-0.11 kg/MT corn kernel.

In preferred embodiments the enzyme composition comprises cellulase obtained from a culture of *Trichoderma reesei*, such as a culture of *Trichoderma reesei* ATCC 26921. Suitable cellulases are available; e.g. from Novozymes A/S under the commercial name Celluclast®.

Polypeptides Having Xylanase Activity

Xylanases are suitable to be applied in the method according to the invention. The xylanase polypeptide may be selected from family GH5, GH10, GH30, GH11, and GH8.

More specific embodiments relates to the method according to the invention, wherein the GH5 xylanase enzyme is selected from the group consisting of:

(a) a polypeptide having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 1;

(b) a variant of the mature polypeptide of SEQ ID NO: 1 comprising a substitution, deletion, and/or insertion at one or more positions; and (c) a fragment of the polypeptide of (a), or (b) that has xylanase activity.

The mature polypeptide is in one embodiment amino acids 25 to 551 of SEQ ID NO: 1.

Another specific embodiment relates to the method according to the invention, wherein the GH10 xylanase is selected from the group consisting of:

(a) a polypeptide having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 2;

(b) a variant of the mature polypeptide of SEQ ID NO: 2 comprising a substitution, deletion, and/or insertion at one or more positions; and (c) a fragment of the polypeptide of (a), or (b) that has xylanase activity.

The mature polypeptide is in one embodiment amino acids 21 to 405 of SEQ ID NO: 2.

Another specific embodiment relates to the method according to the invention, wherein the GH10 xylanase is selected from the group consisting of:

(a) a polypeptide having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 4;

(b) a variant of the mature polypeptide of SEQ ID NO: 4 comprising a substitution, deletion, and/or insertion at one or more positions; and (c) a fragment of the polypeptide of (a), or (b) that has xylanase activity.

The mature polypeptide is in one embodiment amino acids 20 to 319 of SEQ ID NO: 4.

Polypeptides Having Arabinofuranosidase Activity

Another specific embodiment relates to the method according to the invention, wherein the GH62 arabinofuranosidase is selected from the group consisting of:

(a) a polypeptide having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 3;

(b) a variant of the mature polypeptide of SEQ ID NO: 3 comprising a substitution, deletion, and/or insertion at one or more positions; and (c) a fragment of the polypeptide of (a), or (b) that has xylanase activity.

The mature polypeptide is in one embodiment amino acids 17 to 325 of SEQ ID NO: 3.

Sources of Polypeptides Having Xylanase Activity

A polypeptide having xylanase activity may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a bacterial polypeptide. For example, the polypeptide may be a Gram-positive bacterial polypeptide such as a *Bacillus, Chryseobacterium, Clostridium, Enterococcus, Geobacillus, Lactobacillus, Lactococcus, Oceanobacillus, Staphylococcus, Streptococcus*, or *Streptomyces* polypeptide having pectin lyase activity, or a Gram-negative bacterial polypeptide such as a *Campylobacter, E. coli, Flavobacterium, Fusobacterium, Helicobacter, Ilyobacter, Neisseria, Pseudomonas, Salmonella*, or *Ureaplasma* polypeptide.

In one aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* polypeptide.

In another aspect, the polypeptide is a *Streptococcus equisimilis, Streptococcus pyogenes, Streptococcus uberis*, or *Streptococcus equi* subsp. *Zooepidemicus* polypeptide.

In another aspect, the polypeptide is a *Streptomyces achromogenes, Streptomyces avermitilis, Streptomyces coelicolor, Streptomyces griseus*, or *Streptomyces lividans* polypeptide.

The polypeptide may be a fungal polypeptide. For example, the polypeptide may be a yeast polypeptide such as a *Candida, Kluyveromyces, Pichia, Saccharomyces, Schizosaccharomyces*, or *Yarrowia* polypeptide; or a filamentous fungal polypeptide such as an *Acremonium, Agaricus, Alternaria, Aspergillus*, e.g., *Aspergillus niger, Aureobasidium,*

*Botryosphaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces*, e.g., *Talaromyces leycettanus, Thermoascus, Thielavia, Tolypocladium, Trichoderma, Trichophaea, Verticillium, Volvariella*, or *Xylaria* polypeptide.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Enzyme Compositions

An enzyme compositions for use in the method according to the invention may comprise a xylanase polypeptide as the major enzymatic component, e.g., a mono-component composition. Alternatively, the compositions may comprise multiple enzymatic activities, such as one or more (e.g., several) enzymes selected from the group consisting of cellobiohydrolase, cellulase, endoglucanase, and/or arabinofuranosidase.

The compositions may be prepared in accordance with methods known in the art and may be in the form of a liquid or a dry composition. The compositions may be stabilized in accordance with methods known in the art.

The invention is further disclosed in the following numbered embodiments.

Embodiment 1. A method for increasing starch yield and/or gluten yield from corn kernels in a wet milling process, comprising contacting a fiber rich fraction of ground kernels, with an effective amount of $SO_2$, and an effective amount of one or more hydrolytic enzymes, wherein at least one of said hydrolytic enzymes is selected from xylanase and/or cellulase enzymes, during a fiber-washing step.

Embodiment 2. The method according to embodiment 1, wherein the amount of starch and/or gluten released from fiber during the wet milling process is increased compared to a process where no $SO_2$ is present/added.

Embodiment 3. The method according to any of the preceding embodiments, comprising the steps of:

a) soaking the corn kernels in water to produce soaked kernels;

b) grinding the soaked kernels to produce ground kernels;

c) separating germs from the ground kernels to produce a corn kernel mass comprising fiber, starch and gluten;

d) subjecting the resultant corn kernel mass comprising fiber to a fiber washing procedure, thereby separating starch, gluten, and fiber;

wherein at least a xylanase and/or cellulase enzyme(s) and an effective amount of $SO_2$ is present/added before or during step d).

Embodiment 4. The method of any of embodiments 1-3, wherein $SO_2$ is present/added during fiber wash step (d) in amounts of at least 400 ppm, at least 450 ppm, at least 500 ppm, at least 600 ppm, at least 700 ppm, at least 800 ppm.

Embodiment 5. The method of any of the embodiments 1-4, wherein $SO_2$ is present/added during fiber wash in amounts in a range from 400-3000 ppm, 500-2000 ppm, 600-1500 ppm, such as 600-1200 ppm.

Embodiment 6. The method of any of the preceding embodiments, wherein the xylanase is selected from the group consisting of a GH5 polypeptide, GH30 polypeptide, a GH10 polypeptide, a GH11 polypeptide, a GH8 polypeptide or a combination thereof.

Embodiment 7. The method of any of the preceding embodiments, wherein the hydrolytic enzymes comprise one or more cellulases, particularly cellulases obtained from *Trichoderma*, more particularly from *Trichoderma reesei*.

Embodiment 8. The method of embodiment 7, wherein the cellulase(s) comprise(s) one or more enzymes selected from the group consisting of an endoglucanase (EG), and a cellobiohydrolase (CBH).

Embodiment 9. The method of embodiment 8, wherein the cellulase(s) comprise(s) one or more enzymes selected from the group consisting of an endoglucanase, a cellobiohydrolase I, a cellobiohydrolase II, or a combination thereof.

Embodiment 10. The method of any of the preceding embodiments, wherein the hydrolytic enzymes further comprise an arabinofuranosidase.

Embodiment 11 The method of embodiment 10, wherein the arabinofurasnosidase is selected from the group consisting of a GH43 polypeptide, a GH62 polypeptide, and a GH51 polypeptide.

Embodiment 12. The method according to any of embodiments 3-9, wherein said fiber washing procedure comprises the use of a fiber washing system comprising a space (V)/tank configured to provide a total retention time in the fiber washing system of at least 35 minutes and less than 48 hours.

Embodiment 13. The method according to any of the preceding embodiments, wherein the incubation time in said space (V)/tank configured into the fiber washing system is at least 5 minutes and less than 48 hours, such as between 35 minutes and 24 hours, 35 minutes and hours, 35 minutes and 6 hours, 35 minutes and 5 hours, 35 minutes and 4 hours, 35 minutes and 3 hours, 35 minutes and 2 hours, 45 minutes and 48 hours, 45 minutes and 24 hours, 45 minutes and 12 hours, 45 minutes and 6 hours, 45 minutes and 5 hours, 45 minutes and 4 hours, 45 minutes and 3 hours, 45 minutes and 2 hours.

Embodiment 14. The method according to any of the preceding embodiments, wherein the incubation temperature is between 25° C. and 95° C., such as between 25 and 90° C., 25 and 85° C., 25 and 80° C., 25 and 75° C., 25 and 70° C., 25 and 65° C., 25 and 60° C., 25 and 55° C., 25 and 53° C., 25 and 52° C., 30 and 90° C., 30 and 85° C., 30 and 80° C., 30 and 75° C., 30 and 70° C., 30 and 65° C., 30 and 60° C., 30 and 55° C., 30 and 53° C., 30 and 52° C., 35 and 90° C., 35 and 85° C., 35 and 80° C., 35 and 75° C., 35 and 70° C., 35 and 65° C., 35 and 60° C., 35 and 55° C., 35 and 53° C., 35 and 52° C., 39 and 90° C., 39 and 85° C., 39 and 80° C., 39 and 75° C., 39 and 70° C., 39 and 65° C., 39 and 60° C., 39 and 55° C., 39 and 53° C., 39 and 52° C., preferably 46 and 52° C.

Embodiment 15. The method according to any of the preceding embodiments, wherein the level of $SO_2$ present/added during fiber wash results in the same extraction yield of starch and gluten while reducing the required contact time between hydrolytic enzyme and ground corn kernel mass compared to a method where $SO_2$ levels are below 400 ppm.

Embodiment 16. The method according to any of the preceding embodiments, wherein the one or more hydrolytic enzymes is expressed in an organism with a cellulase background, such as *Trichoderma reesei.*

Embodiment 17. The method according to any of the preceding embodiments, wherein the one or more hydrolytic enzymes are purified.

Embodiment 18. The method according to any of the preceding embodiments, wherein the one or more hydrolytic enzymes is/are in a liquid composition.

Embodiment 19. The method according to any of the preceding embodiments, wherein the one or more hydrolytic enzymes is/are in a solid composition.

Embodiment 20. The method according to any of the preceding embodiments, wherein the effective amount of one or more hydrolytic enzymes admixed/contacted with one or more fractions of said ground corn kernel mass, is between 0.005-0.5 kg enzyme protein/metric tonne corn kernels entering the wet milling process.

Embodiment 21. The method according to any of the preceding embodiments, wherein the source of $SO_2$ is sodium metabisulfite ($Na_2S_2O_5$), and/or addition of $SO_2$ gas.

Embodiment 22. The method according to any of the preceding embodiments wherein the xylanase is selected from the group consisting of:

(a) a polypeptide having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 1;

(b) a variant of the mature polypeptide of SEQ ID NO: 1 comprising a substitution, deletion, and/or insertion at one or more positions; and (c) a fragment of the polypeptide of (a), or (b) that has xylanase activity.

Embodiment 23. The method of embodiment 22, wherein the mature polypeptide is amino acids 1 to 551 of SEQ ID NO: 1.

Embodiment 24. The method according to any of the preceding embodiments wherein the xylanase is selected from the group consisting of:

(a) a polypeptide having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 2;

(b) a variant of the mature polypeptide of SEQ ID NO: 2 comprising a substitution, deletion, and/or insertion at one or more positions; and (c) a fragment of the polypeptide of (a), or (b) that has xylanase activity.

Embodiment 25. The method of embodiment 24, wherein the mature polypeptide is amino acids 21 to 405 of SEQ ID NO: 2.

Embodiment 26. The method of any of the preceding embodiments, wherein the arabinofuranosidase is selected from the group consisting of:

(a) a polypeptide having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 3;

(b) a variant of the mature polypeptide of SEQ ID NO: 3 comprising a substitution, deletion, and/or insertion at one or more positions; and (c) a fragment of the polypeptide of (a), or (b) that has xylanase activity.

Embodiment 27. The method of embodiment 26, wherein the mature polypeptide is amino acids 17 to 325 of SEQ ID NO: 3.

Embodiment 28. The method according to any of the preceding embodiments wherein the xylanase is selected from the group consisting of:

(a) a polypeptide having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 4;

(b) a variant of the mature polypeptide of SEQ ID NO: 4 comprising a substitution, deletion, and/or insertion at one or more positions; and (c) a fragment of the polypeptide of (a), or (b) that has xylanase activity.

Embodiment 29. The method of embodiment 28, wherein the mature polypeptide is amino acids 20 to 319 of SEQ ID NO: 4.

Embodiment 30. The method according to any of the preceding embodiments, wherein the celullases are derived from *Trichoderma reesei.*

The invention is further illustrated by the following examples.

EXAMPLES

Enzymes:

GH5 Xylanase A: GH5 xylanase derived from *Chryseobacterium* sp-10696 and disclosed as SEQ ID NO: 1

Cellulase A: A whole cellulase derived from *Trichoderma reesei*. This cellulase composition will comprise all cellulase activities expressed in *T. reesei*; e.g., endoglucanases, and cellobiohydrolases.

Examples 1

10-g fiber assay is performed with 5% fiber dry substance incubating at pH4.0, 50° C. for 150 minutes at dose of 200 μg or 300 μg enzyme protein per gram fiber dry substance, using a blend including Cellulase A and GH5 Xylanase A, in combination with either 400 ppm or 800 ppm hydrogen sulfite ($HSO_3^-$). Blend consists of 8% of GH5 Xylanase A, and 92% of Cellulase A based on enzyme protein. Hydrogen sulfite is generated by adding sodium metabisulfite ($Na_2S_2O_5$) into the buffer following the reaction of $Na_2S_2O_5+H_2O \rightarrow 2Na^++2HSO_3^-$. For comparison, blend containing 92% Cellulase A and 8% GH5 Xylanase A only (no $SO_2$) at both low dose (200 μg EP/g-ds fiber) and high dose (300 μg EP/g-ds fiber) were included. The corn fiber with 17.77% residual starch and 9.88% residual protein was used as substrate in the fiber assay. Release of starch+gluten (dry substance) as well as individual protein from corn fiber at the specified treatment below was measured.

TABLE 1

Starch and gluten yield with and without enzymatic treatment

| Treatments | Dose (μg enzyme protein/g-ds Fiber) | Starch + Gluten Recovered | Individual Protein Recovered |
|---|---|---|---|
| No Enzyme | 0 | 10.05% | 0.65% |
| Cellulase A + GH5 Xylanase A | 200 | 12.20% | 1.02% |
| Cellulase A + GH5 Xylanase A + $HSO_3^-$ (400 ppm) | 200 | 14.45% | 1.60% |
| Cellulase A + GH5 Xylanase A + $HSO_3^-$ (800 ppm) | 200 | 15.00% | 1.74% |
| Cellulase A + GH5 Xylanase A | 300 | 14.65% | 1.48% |
| Cellulase A + GH5 Xylanase A + $HSO_3^-$ (400 ppm) | 300 | 15.35% | 1.82% |

Therefore, the addition of Hydrogen sulfite on top of Cellulase A+GH5 Xylanase A can significantly increase the yield of starch+gluten as well as protein in corn wet-milling process.

Example 2

A 10-g fiber assay generally includes incubating wet fiber samples obtained from wet-milling plant, in the presence of enzymes, at conditions relevant to the process (pH 4, temp around 50° C.) and over a time period of between 1 to 4 hrs. After incubation the fiber is transferred and pressed over a 75 micron screen where the filtrates consisting mainly of the separated starch and gluten are then collected. A number of washes are done over the screen, and the washing are collected together with the initial filtrate. The collected filtrates are allowed to sit overnight letting the insoluble settle to the bottom of the flask. The bulk of the supernatant is aspirated via vacuum and the rest of the insolubles are then centrifuged in 50 ml conical tubes and the supernatant is decanted leaving a wet insoluble pellet. The wet insoluble pellet is lyophilized o/n to complete dryness. This insoluble dry mass is weighed to determine % insoluble yield and then analyzed for total nitrogen content (protein) via Leco analysis.

This 10-g fiber assay was performed with 6.4% fiber dry substance incubating at pH 4.0, 48° C. for 240 minutes at dose of 5000 μg enzyme protein per gram fiber dry substance, using a blend including Cellulase A and GH5 Xylanase A. The blend consists of 10% of GH5 Xylanase A, and 90% of Cellulase A based on enzyme protein. This blend was tested both in as-is substrate and in substrate sheared (homogenized) for 3 minutes in a blender. The homogenized substrate was treated with the enzyme blend with and without 1000 ppm SO2 (added from a 20× dilution of 1.48 g Na metabisulfate dissolved in 50 ml water) and a no enzyme treatment. The as-is substrate was treated with the enzyme blend both with and without 1000 ppm SO2 while two no enzyme treatments were performed with and without 1000 ppm SO2. The weights of insoluble mass (starch and gluten) and insoluble protein (gluten) released by the specified treatments are given below.

TABLE 2

Results

| | Treatement | insolubles % of starting fiber | Insoluble Protein % of starting fiber | % CGM increase over respective no ezyme control |
|---|---|---|---|---|
| homogenized | no enzyme | 37.1% | 1.9% | |
| | Xylanase A | 38.3% | 3.3% | 0.23% |
| | Xylanase A + SO2 | 39.7% | 4.0% | 0.35% |
| as is | no enzyme | 29.6% | 1.2% | |
| | no enzyme + SO2 | 29.5% | 1.5% | 0.04% |
| | Xylanase A | 36.5% | 3.4% | 0.36% |
| | Xylanase A + SO2 | 36.9% | 3.7% | 0.42% |

What is claimed is:

1. A wet milling process, comprising the steps of:

a) soaking corn kernels in water to produce soaked kernels; a)

b) grinding the soaked kernels to produce ground kernels; b)

c) separating germs from the ground kernels to produce a corn kernel mass comprising c) fiber, starch and gluten;

d) subjecting the resultant corn kernel mass comprising fiber to a fiber washing procedure, thereby separating starch, gluten, and fiber;

wherein step d) further comprises contacting a fiber rich fraction of ground corn kernels with one or more hydrolytic enzymes selected from a xylanase, a cellulase, or a xylanase and a cellulase and at least 500 ppm of $SO_2$ during step d), and wherein the amount of starch, gluten or both starch and gluten released from fiber during the wet milling process is increased compared to a process where no $SO_2$ is added during step d).

2. The method according to claim 1, wherein $SO_2$ is present or added during fiber wash step (d) in amounts of at least 600 ppm, at least 700 ppm, or at least 800 ppm.

3. The method according to claim 1, wherein $SO_2$ is present or added during fiber wash in an amount of 500-2000 ppm.

4. The method according to claim 1, wherein the xylanase is selected from the group consisting of a GH5 xylanase, a GH30 xylanase, a GH10 xylanase, a GH11 xylanase, a GH8 xylanase, and a combination thereof.

5. The method according to claim 1, wherein the one or more hydrolytic enzymes comprise one or more cellulases.

6. The method according to claim 5, wherein the cellulase(s) comprise(s) one or more enzymes selected from the group consisting of an endoglucanase (EG), and a cellobiohydrolase (CBH).

7. The method according to claim 6, wherein the cellulase(s) comprise(s) one or more enzymes selected from the group consisting of an endoglucanase, a cellobiohydrolase I, a cellobiohydrolase II, and a combination thereof.

8. The method according to claim 1, wherein the hydrolytic enzymes further comprise an arabinofuranosidase.

9. The method according to claim 8, wherein the arabinofuranosidase is selected from the group consisting of a GH43 polypeptide, a GH62 polypeptide, and a GH51 polypeptide.

10. The method according to claim 1, wherein said fiber washing procedure comprises a fiber washing system comprising a space for providing a total retention time in the fiber washing system of at least 35 minutes and less than 48 hours.

11. The method according to claim 10, wherein an incubation time in said space in the fiber washing system is between 35 minutes and 12 hours.

12. The method according to claim 11, wherein an incubation temperature in said space in the fiber washing system is between 39° C. and 55° C.

13. The method according to claim 1, wherein the $SO_2$ present or added during fiber wash results in the same extraction yield of starch and gluten while reducing the required contact time between the one or more hydrolytic enzymes and the corn kernel mass compared to a method where $SO_2$ levels are below 400 ppm.

14. The method according to claim 1, wherein the one or more hydrolytic enzymes is expressed in an organism with a *Trichoderma reesei* cellulase background.

15. The method according to claim 1, wherein the one or more hydrolytic enzymes are purified.

16. The method according to claim 1, wherein the one or more hydrolytic enzymes is contacted with the fiber rich fraction of ground corn kernels in an amount between 0.005-0.5 kg enzyme protein/metric tonne corn kernels entering the wet milling process.

17. The method according to claim 1, wherein the source of $SO_2$ is sodium metabisulfite ($Na_2S_2O_5$), addition of $SO_2$ gas, or sodium metabisulfite and addition of $SO_2$ gas.

* * * * *